United States Patent [19]
Zablotsky et al.

[11] Patent Number: 5,450,858
[45] Date of Patent: Sep. 19, 1995

[54] LUMBOSACRAL BELT

[76] Inventors: Theodore J. Zablotsky, 44 Miamis Rd., West Hartford, Conn. 06117; Charles Zablotsky, 5821 Quiet Oak La., Fort Lauderdale, Fla. 33312; Jerome M. True, 5760 SW. 14th St., Plantation, Fla. 33317; Paul E. Gallo, 21181-C Clubside Dr., Boca Raton, Fla. 33434

[21] Appl. No.: 175,667

[22] Filed: Dec. 30, 1993

Related U.S. Application Data

[63] Continuation of Ser. No. 12,395, Feb. 2, 1993, abandoned.

[51] Int. Cl.$^6$ ............................................. A61F 5/02
[52] U.S. Cl. ........................................ 128/876; 602/13; 602/19; 2/338; 600/15
[58] Field of Search ........ 128/869, 875, 876, DIG. 15, 128/DIG. 20; 2/2, 338, DIG. 3; 600/15; 602/13, 19

[56] References Cited

U.S. PATENT DOCUMENTS

| | | | |
|---|---|---|---|
| 178,611 | 6/1876 | Dye | 600/15 |
| 658,027 | 9/1900 | Steiger | 600/15 |
| 1,050,280 | 1/1913 | Krüger | 600/15 |
| 2,028,060 | 1/1936 | Gilbert | 602/13 |
| 4,178,923 | 12/1979 | Curlee | 602/13 |
| 4,480,596 | 11/1984 | Shumiyashu | 600/15 |
| 4,549,532 | 10/1985 | Baermann | 600/15 |
| 4,682,588 | 7/1987 | Curlee | 602/13 |
| 4,703,750 | 11/1987 | Sebastian et al. | 128/78 |
| 5,017,185 | 5/1991 | Baermann | 600/15 |
| 5,045,050 | 9/1991 | Liboff | 600/15 |
| 5,067,940 | 11/1991 | Liboff | 600/15 |
| 5,195,948 | 3/1993 | Hill | 602/19 |
| 5,205,814 | 4/1993 | Lundrigan | 128/DIG. 20 |

FOREIGN PATENT DOCUMENTS

| | | | |
|---|---|---|---|
| 2733982 | 2/1979 | Germany | 600/15 |
| 3346293 | 7/1985 | Germany | 600/15 |
| 8203178 | 9/1982 | WIPO | 600/15 |

Primary Examiner—Michael A. Brown
Attorney, Agent, or Firm—Vickers, Daniels & Young

[57] ABSTRACT

An air inflatable belt worn by a person for support in the lumbar and sacral regions of the body has an inner wall, which faces the body of the person, provided with one or more permanent magnet arrangements producing magnetic fields directed toward the person's body. The permanent magnet arrangements may be provided by one or more flexible magnetic sheets received in a pocket or pockets on the inner wall of the belt, or by permanent magnet particles embedded in the inner wall of the belt and magnetized to provide desired magnetic field patterns. The belt includes an inflatable bladder or bladders which may be removably supported on the belt.

30 Claims, 5 Drawing Sheets

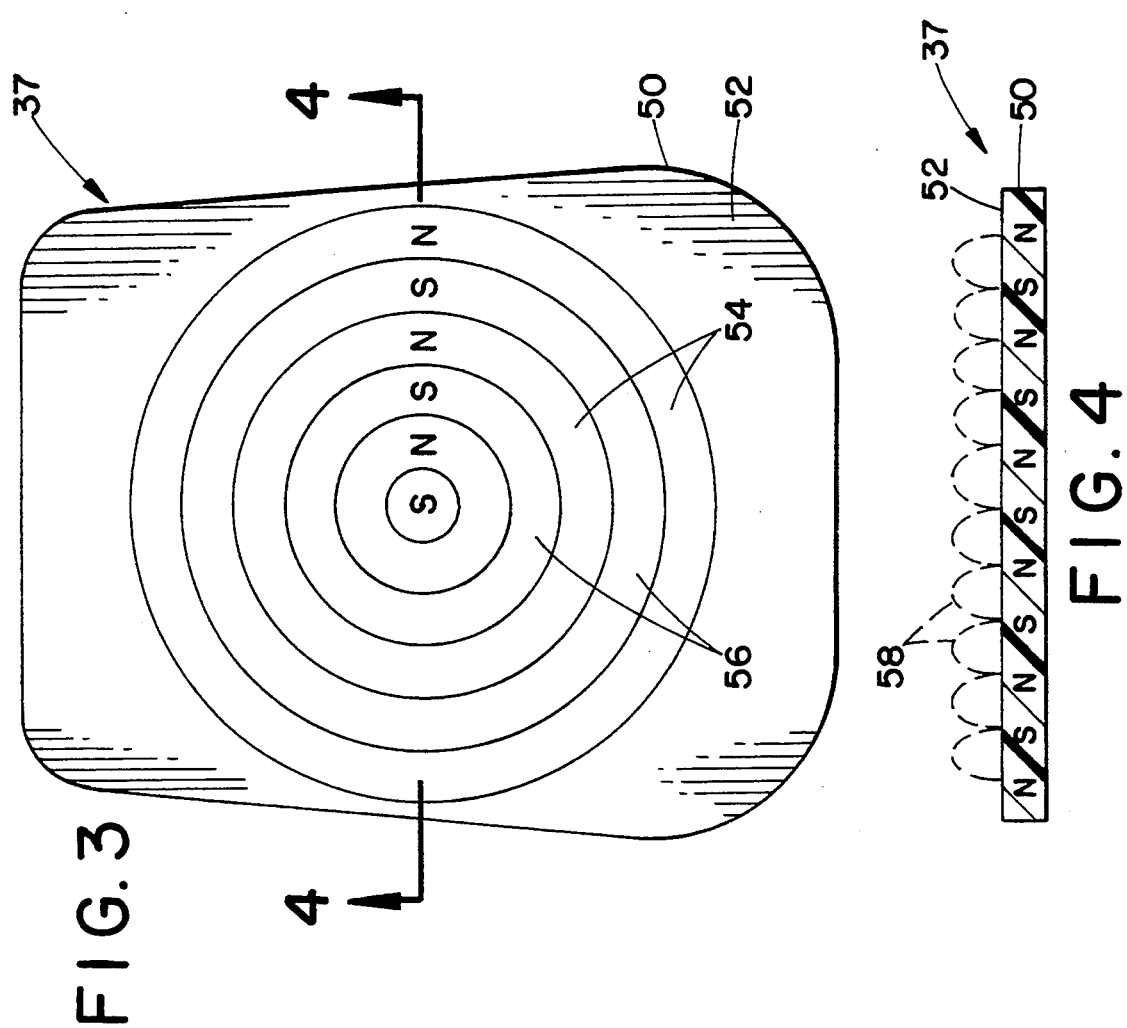
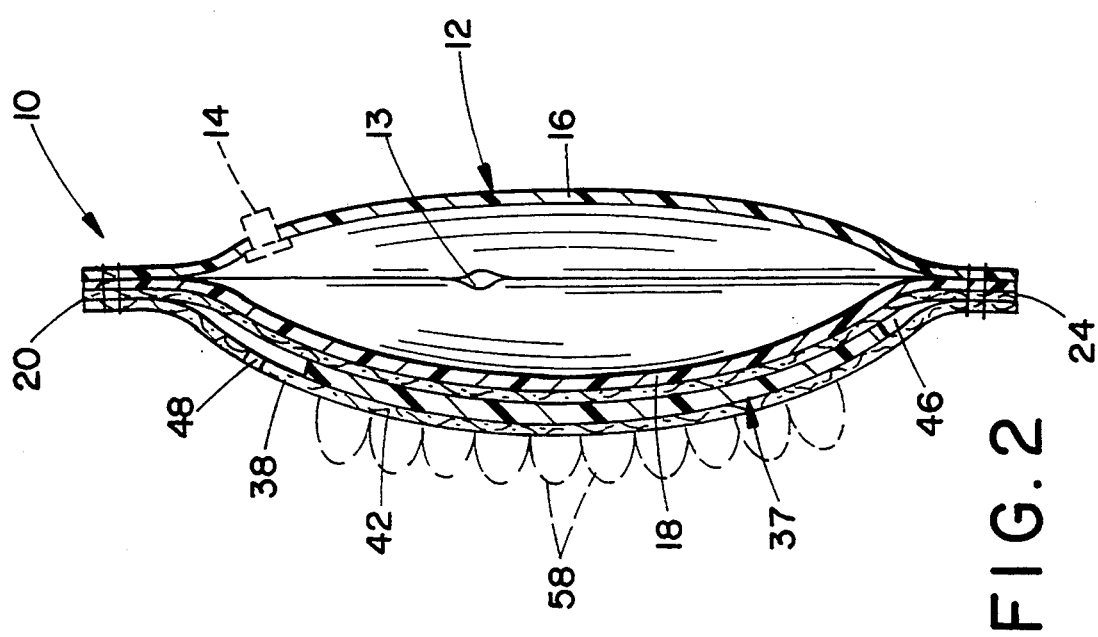

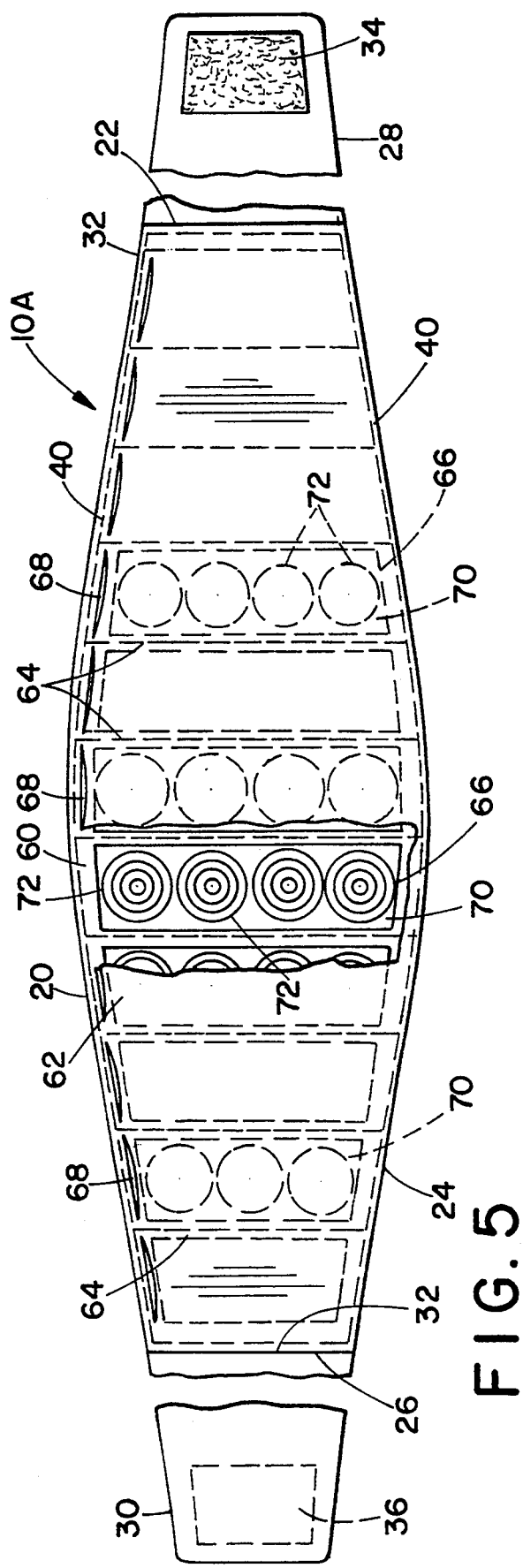
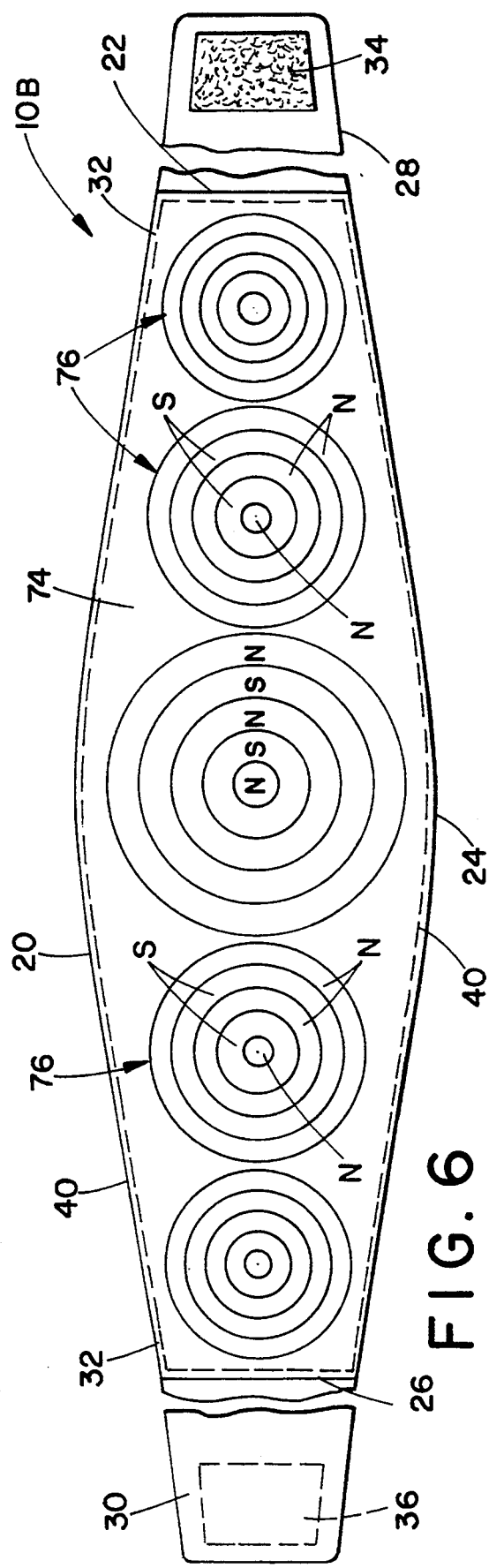

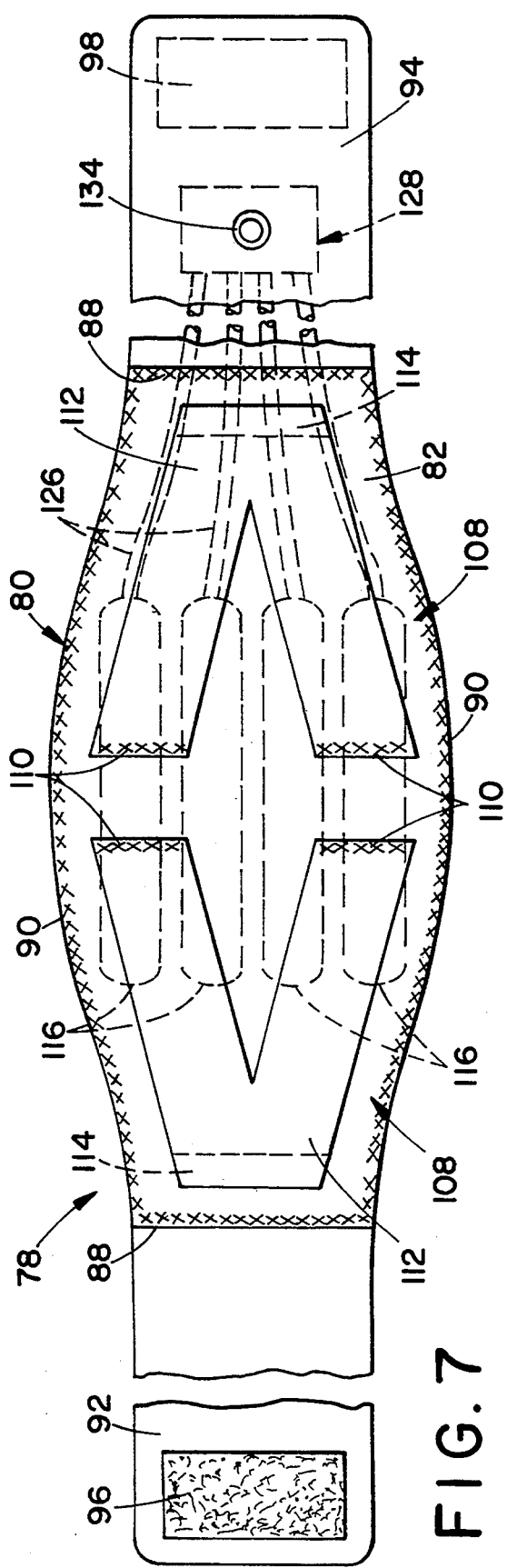
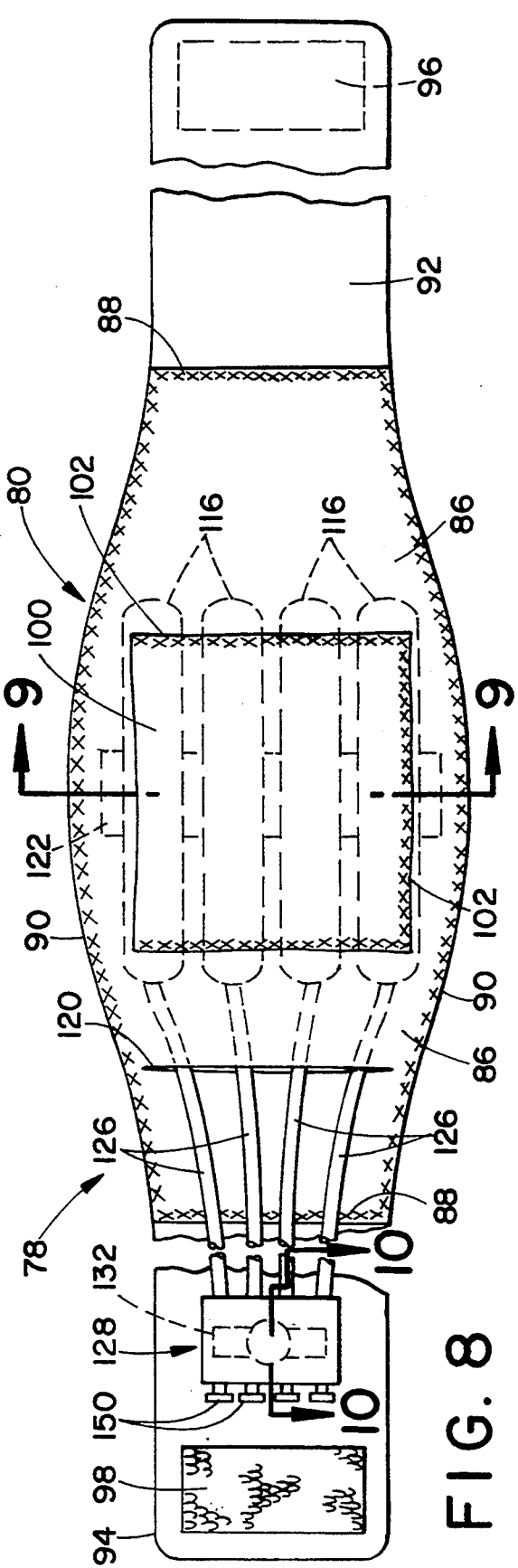

LUMBOSACRAL BELT

This is a continuation of application Ser. No. 012,395, filed Feb. 2, 1993, now abandoned.

BACKGROUND OF THE INVENTION

Air inflatable belts worn around the waist of a person are well known as therapeutic appliances for reducing and/or protecting against incidents of pain resulting from spasms and/or fatigue of the muscles and nerves in the lumbar or lumbar and sacral regions of the spine. Such belts include one or more air bladders which are inflatable through the use of a detachable aspirator bulb as disclosed, for example, in U.S. Pat. No. 4,703,750 to Sebastian et al which is incorporated by reference herein for background information. The opposite ends of the belt are adapted to interengage, such as by VELCRO fastening components to releasably hold the belt about a person's body.

In use, the belt is attached in place about the person's body with the bladder or bladders overlying the lumbar and sacral regions, and the bladder or bladders are inflated to provide the amount of pressure desired by the wearer. The pressure provides mechanical support for the muscles and ligaments in the lower spine area and provides static stretch to the erector spinae muscle and aids in the prevention and elimination of spasms by maintaining these muscles in a more stretched and relaxed state.

SUMMARY OF THE INVENTION

In accordance with the present invention, inflatable belts of the the foregoing character are adapted to be provided with a permanent magnet arrangement or arrangements to promote muscle relaxation and a reduction in muscle spasms and fatigue by promoting blood circulation in the lumbar or lumbar and sacral regions. More particularly in this respect, the inner side of the inflatable belt which faces the body of a person wearing the belt is provided with the permanent magnet arrangement or arrangements which produce magnetic fields directed outwardly from the inner side of the belt and thus toward the person's body. The permanent magnet arrangement or arrangements may be provided in any suitable manner and, preferably, are provided by relatively thin magnetic sheet material removably received in one or more pockets provided therefor on the inner side of the belt, or by permanent magnet particles of a ferrite material embedded in the material providing the inner side of the belt and magnetized to provide adjacent areas of opposite polarity.

In accordance with one aspect of the invention, the provision of the belt with a plurality of pockets advantageously enables selectivity with respect to positioning a magnet arrangement or arrangements relative to the opposite ends of the belt and thus different areas of the back of a person wearing the belt and/or selectivity with respect to the flux density of the magnet arrangement or arrangements used with the belt. Thus the position and number of magnets and the strengths thereof can be customized for each patient. This enables different pain patterns to be effectively treated with variations of magnet placement and strength.

In accordance with another aspect of the invention, a plurality of bladders associated with a belt are independently inflatable. The use of a magnet or magnetic arrangements in conjunction with selectably inflatable bladders in the belt provides for the user customizing stabilization on varying degrees of firmness or softness and stabilization of specific vertebral levels by selectively inflating the bladders. At the same time the selectably inflatable bladders enable providing uniform pressure for conforming the magnet or magnets to the contour of the user's back to optimize the effect thereof. In connection with yet another aspect of the invention, the inflatable bladders are removably supported on a belt. This advantageously provides selectability with respect to using the belt with a magnet or magnets alone or in combination with inflatable bladders.

With regard to the magnets, a variety of patterns can be employed with respect to the geometry of the adjacent north and south poles. For example, the latter can be defined by linear, parallel strips of alternate polarity disposed parallel, perpendicular or in any other desired orientation relative to the direction between the opposite ends of the belt and, in connection with a pocketed belt, magnetic sheet material having such a pole pattern can be inserted into two or more of the pockets to provide the belt with a combination of the possible orientations, thus to provide the belt with areas in which the flux fields are at different angles to the direction between the opposite ends of the belt.

While the above and other pole patterns can be employed, it is preferred to provide pole patterns which, for a given magnet arrangement, have the north and south poles arranged in a geometric pattern which establishes magnetic fields having angularities with respect to a line traversing the plane of the surface of the permanent magnet arrangement. A number of pole patterns of the foregoing character are illustrated and described in U.S. Pat. No. 4,549,532 to Baermann, which patent is hereby incorporated herein by reference for background information. Pole patterns of such geometry are preferred in connection with the present invention in that the angularities of the magnetic fields provide for the lines of flux to traverse areas of the person's body in a desired direction regardless of the orientation of the magnet arrangement on the belt. In this respect, for example, if a blood vessel extends vertically of a person's back the preferred direction for the field flux relative thereto is horizontal, and horizontal lines of flux are produced with the geometries shown in the Baermann patent, regardless of the orientation of the magnetic sheet material in the plane thereof. The most preferred pole pattern for use in connection with the present invention is that in which the north and south poles are arranged in concentric rings of alternating polarity.

It is accordingly an outstanding object of the present invention to provide an improved therapeutic belt worn about the lower back portion of a person as a preventative or rehabilitative device for muscular lower back discomfort.

A further object is the provision of an improved air inflatable therapeutic belt of the foregoing character.

Another object is the provision of belts of the foregoing character with a magnet arrangement or arrangements on the side of the belt facing the body of the wearer to promote blood circulation in the area of the wearer's body facing the magnet arrangement or arrangements.

Yet another object is the provision of a belt of the foregoing character wherein the position and number of magnets relative to the opposite ends and/or the flux density of the magnets can be selectively changed.

Still another object of the provision of an inflatable belt of the foregoing character wherein the inflatable bladder or bladders are removably supported on the belt.

A further object is the provision of an inflatable belt having a plurality of bladders which are independently inflatable.

Still a further object is the provision of a belt of the foregoing character wherein the magnet or magnets provide universal direction with respect to magnetic flux lines generated thereby.

BRIEF DESCRIPTION OF THE DRAWING

The foregoing objects, and others, will in part be obvious and in part pointed out more fully hereinafter in conjunction with the written description of preferred embodiments of the invention illustrated in the accompanying drawings in which:

FIG. 2 is a cross-sectional elevation view taken along line 2—2 in FIG. 1;

FIG. 3 is a plan view of a preferred magnetic sheet for the belt;

FIG. 4 is a cross-sectional elevation view of the magnetic sheet taken along line 4—4 in FIG. 3;

FIG. 5 is an elevation view of another embodiment of the belt in accordance with the present invention;

FIG. 6 is an elevation view of a further embodiment of a belt in accordance with the present invention;

FIG. 7 is an elevation view of one side of yet another embodiment of a belt in accordance with the invention;

FIG. 8 is an elevation view of the other side of the belt shown in FIG. 7;

DESCRIPTION OF PREFERRED EMBODIMENTS

Figure 1:
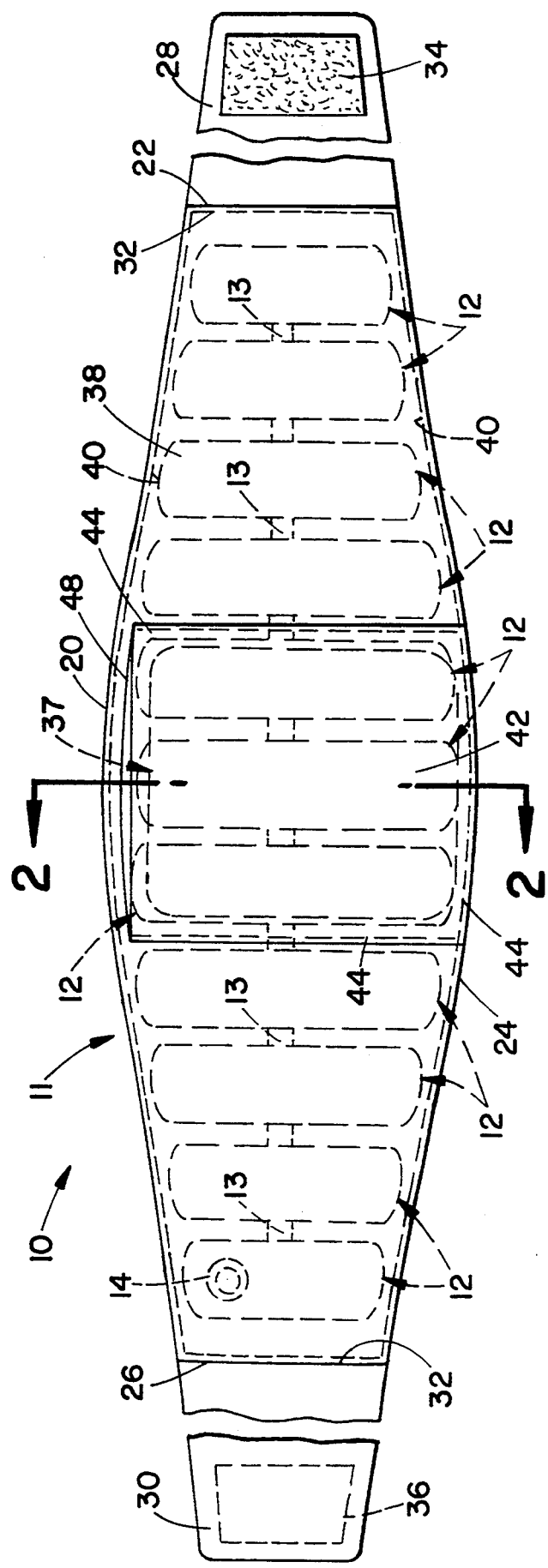
FIG. 1 is an elevation view of an air inflatable belt in accordance with the present invention.

Referring now in greater detail to the drawings wherein the showings are for the purpose of illustrating preferred embodiments of the invention only, and not for the purpose of limiting the invention, FIGS. 1 and 2 illustrate a lumbar belt 10 comprising an inflatable section 11 defined by eleven bladders 12 interconnected by passageways 13 therebetween. One of the bladders has an air valve 14 by which the bladders are adapted to be inflated through the use of a detachable aspirator bulb, not shown. Bladders 12 are provided by suitably uniting a pair of sheets 16 and 18 of nylon or vinyl material of low stretchability. The sheets can be united such as by heat sealing the sheets about the peripheral edges 20, 22, 24 and 26 thereof and in the areas within the peripheral edges which bound the individual bladders 12 and passageways 13 therebetween. Belt ends 28 and 30 extend respectively from ends 22 and 26 of bladder section 11 and are connected thereto such as by stitching 32. Ends 28 and 30 are preferably of a breathable, somewhat elastic neoprene and are adapted to be releasably interconnected when the belt is wrapped around a wearer's body such as by VELCRO components 34 and 36 thereon. Inner sheet 18 of bladder section 11 faces the body of a wearer when the belt is in place about the wearer's waist.

In accordance with the present invention, belt 10 is provided with a permanent magnet arrangement overlying bladder section 11 for producing magnetic field lines directed outwardly from inner sheet 18 toward the body of the person wearing the belt. In the embodiment illustrated in FIGS. 1-4, the permanent magnet arrangement comprises a magnetic sheet 37, described in greater detail hereinafter, supported adjacent the outer side of sheet 18. More particularly in this respect, a sheet 38 of moisture absorbing, wicking fabric coextensively overlies and is secured to bladder section 11 by stitching 32 at the opposite ends 22 and 26 of the bladder section and by stitching 40 along top and bottom edges 20 and 24 of the bladder section. A pocket sheet 42 of the wicking material is attached to sheet 38 between the top and bottom edges thereof such as by stitching 44 along the opposite sides and bottom of sheet 42. Sheet 42 provides a pocket 46, and the upper edge of sheet 42 provides an opening 48 into the pocket to facilitate the insertion and removal of magnetic sheet 37.

Preferably, as shown in FIGS. 3 and 4, magnetic sheet 37 comprises a sheet 50 of flexible, rubber-like thermoplastic material having an active surface 52 intended to face outwardly of pocket 46 and thus toward the body of the wearer of the belt. Permanent magnetic particles of barium ferrite or strontium ferrite, for example, are, in a well known manner, embedded in active surface 52 of sheet 50 and selectively magnetized to establish a plurality of alternating north poles 54 and south poles 56 providing magnetic field lines between adjacent poles having the direction indicated by the curved broken lines 58 in FIGS. 2 and 4. Preferably, as will be apparent from FIG. 3, the particles in sheet 50 are magnetized to establish a plurality of concentric rings providing the alternating north and south poles 54 and 56, whereby it will be appreciated that the direction of magnetic field lines 58 is radially of the concentric rings and that the field lines extend circumferentially about the south pole providing the center of the concentric ring arrangement. Thus, it will be further appreciated that the magnetic fields have angularities with respect to a line traversing surface 52. This is advantageous from the standpoint that it provides universal direction of the magnetic field with respect to the area of the wearer's body facing the magnetic sheet. Preferably, sheet 50 is of a thickness from about 0.75 to 1.5 millimeters and the magnetic particles are sufficient to provide a field flux density between about 300 to 500 Gauss. The use of the pocket removably receiving the magnet sheet advantageously enables selectivity with respect to the geometry of the magnetic field or fields of the magnet sheet to be used and/or the strength of the field. Moreover, the flexible magnetic sheet is adjacent the inflatable bladders 12 therebehind and this advantageously provides for the magnet to be pressed against the user when the bladder is inflated. Further, while it is preferred to use an anti-fungul, anti-bacterial moisture absorbing wicking fabric to provide sheet 38 and pocket 42 so as to prevent excessive moisture and organism build-up, it will be appreciated that other materials can be used. While a single pocket is shown, it will be appreciated that pockets can be provided corresponding to others of the bladders 12 to optimize selectivity with respect to placement of magnetic sheets relative to a wearer's back.

Another embodiment of an air inflatable belt in accordance with the present invention is illustrated in FIG. 5 and designated generally by the numeral 10A. While not shown in detail, for purposes of clarity, the bladder section of belt 10A is the same as that of belt 10 described above. Also, belt 10A is otherwise structurally similar to the belt described hereinabove in connection with FIGS. 1 and 2 of the drawing, and like numerals appear in FIG. 5 to designate corresponding parts of the belt. In this embodiment, the inner sheet 18 of the bladder section is covered with a pair of sheets 60 and 62 of moisture absorbing wicking fabric which coextensively overlie the inner sheet of the bladder section between peripheral edges 20, 22, 24 and 26 thereof. Inner sheet 60 is attached to the bladder section by stitching 32 at the opposite ends 22 and 26 thereof and by stitching 40 along top and bottom edges 20 and 24. Outer sheet 62 is stitched at its opposite ends to the inner sheet of the bladder section by stitching 32 and is stitched at its bottom end along bottom edge 24 of the bladder section by stitching 40. The upper end of sheet 62 is not stitched along upper edge 20 of the bladder section, and sheets 60 and 62 are stitched together along a plurality of stitch lines 64 extending in the direction between top and bottom edges 20 and 24 of the bladder section to provide a plurality of pockets 66 having corresponding open upper ends 68 enabling the pockets to selectively and removably receive a magnet sheet 70. Eleven pockets 66 are provided, each overlying one of the eleven bladders in the bladder section.

In the embodiment of FIG. 5, each of the magnet sheets 70 is in the form of a generally rectangular sheet of non-magnetic material similar to sheet 50 shown in FIG. 4 and the active surface of which is provided with permanent magnet particles of ferrite material embedded therein and magnetized to produce a plurality of geometrical patterns 72 in different areas along the length thereof. Preferably, the geometrical patterns are formed by concentric rings of alternating polarity. The provision of the plurality of pockets in this respect advantageously enables selectivity with respect to both the positioning of magnet sheets relative to the lower back of a person wearing the belt and the strength of the magnetic field or fields in selected areas of the wearer's back. Further, while the magnet sheets are preferably defined by a single sheet having a plurality of geometric patterns, it will be appreciated that each geometric pattern can be provided on a corresponding sheet, whereby each pocket could receive one or more of the individual magnet sheets.

FIG. 6 illustrates a further embodiment of a lumbar belt in accordance with the present invention, designated generally by the numeral 10B, and which is structurally similar to belt 10 illustrated in FIG. 5 of the drawing, whereby like numerals appear in FIG. 6 to designate corresponding parts of the belt. Again, as shown in FIG. 5, the bladder section is the same as in FIGS. 1 and 2 for belt 10 and is not shown in FIG. 6 for purposes of clarity. In this embodiment, inner sheet 18 of the bladder section is covered with a sheet 74 of a suitable synthetic rubber-like material such as neoprene which coextensively overlies the bladder section and is secured thereto by stitching 32 and 40. The permanent magnet arrangement for belt 10B is provided by embedding permanent magnet particles of a ferrite material in the surface of sheet 74 facing the wearer of the belt and magnetizing the particles in a plurality of areas between the opposite ends of sheet 74 to provide geometric patterns 76 of alternating north and south polarity. Preferably, as will be apparent from FIG. 6, the north and south poles of each pattern 76 formed by concentric rings of alternating polarity. While the preferred pattern is formed by concentric rings of alternating polarity, it will be appreciated that other patterns can be used, including linear parallel strips of alternating polarity but, preferably, arranged in geometric patterns which establish magnetic fields having angularities with respect to the line traversing the surface of the permanent magnet arrangement facing the wearer of the belt.

Yet another embodiment of a lumbar belt in accordance with the present invention is illustrated in FIGS. 7-10 of the drawing. In this embodiment, the belt is designated generally by numeral 78 and is structured so as to provide a removable inflatable bladder section and to accommodate a removable magnet sheet or sheets.. More particularly in this respect, the belt includes a brace section 80 comprising a pair of mesh fabric sheets 82 and 84 of rubber corded nylon, for example, and a sheet of moisture absorbing wicking fabric 86, all of which sheets are of like contour and are secured together such as by stitching 88 at the opposite ends of brace section 80 and stitching 90 along the top and bottom edges of the brace section. As in the earlier embodiments, belt ends 92 and 94 of a breathable, somewhat elastic neoprene material extends from the opposite ends of brace section 80 and are secured thereto by stitching 88. Further as in the earlier embodiments, belt ends 92 and 94 are adapted to be releasably interconnected when the belt is wrapped around a wearer's body such as by VELCRO components 96 and 98 thereon.

Wicking material sheet 86 faces the body of a person wearing the belt and is provided with a pocket sheet 100 of moisture absorbing wicking material which is secured to sheet 86 by stitching 102 along the opposite side and bottom edges of the pocket. Pocket sheet 100 provides a pocket 104 having an open upper end 106 adapted to receive a magnet such as that shown in FIG. 3 of the drawing, for example. Sheet 82 faces outwardly of the wearer's body and, preferably, is provided with a pair of V-shaped elastic tension straps 108 having inner ends secured to sheets 82 and 84 by stitching 110 and having outer ends 112 each detachably secured to outer sheet 82 such as by a VELCRO fastening arrangement 114 therebetween. Elastic tension straps 108 enable the wearer of the belt to adjust the tension of the belt and thus the pressure thereof against the back when the belt is applied about the waist.

Figure 10:
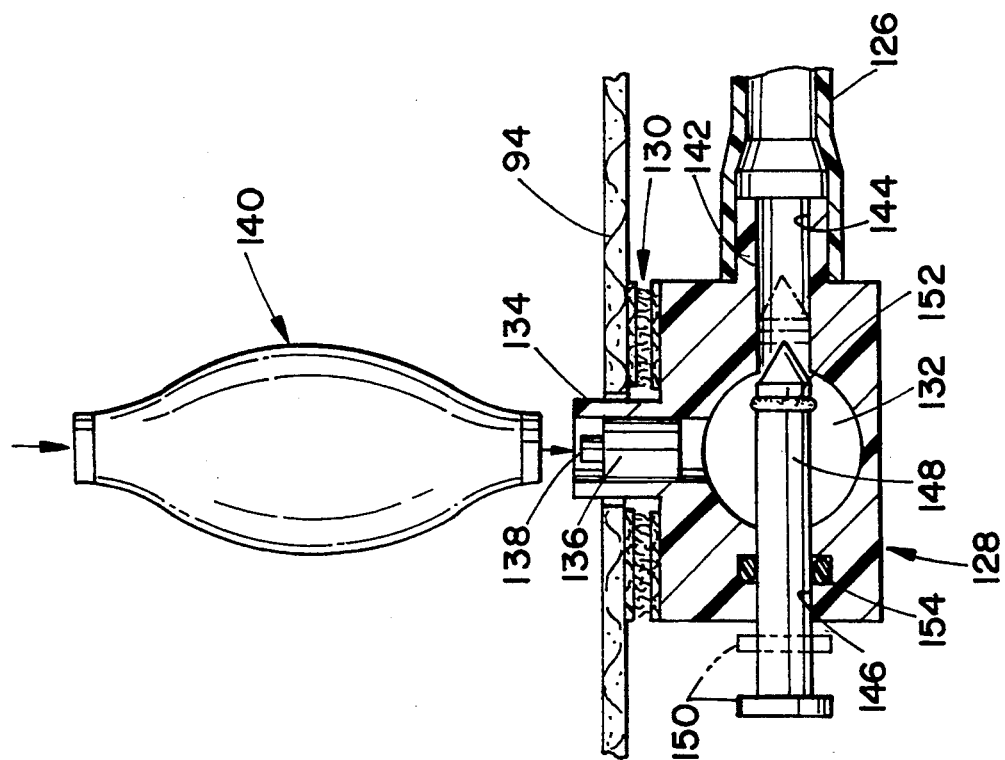
FIG. 10 is a cross-sectional view of the valve block of the belt taken along line 10—10 in FIG. 8.
Figure 9:
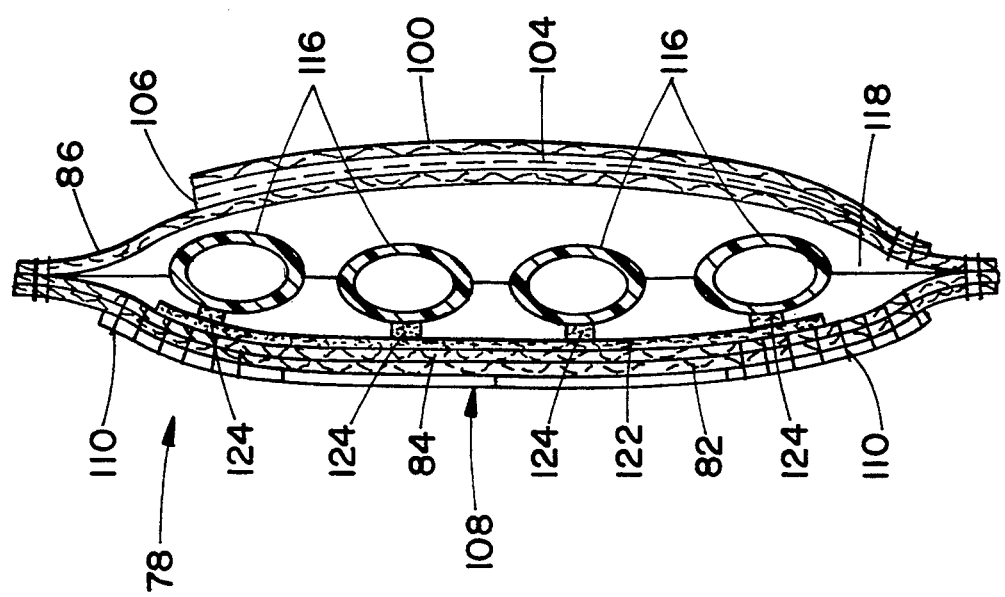
FIG. 9 is a sectional elevation view of the belt taken along line 9—9 in FIG. 8.

Further in accordance with this embodiment, belt 78 is provided with a removable inflatable bladder assembly comprising a plurality of inflatable bladders 116 removably supported in a pocket 118 between wicking sheet 86 and inner mesh fabric sheet 84 and to which access is provided such as by a vertical slit 120 in wicking sheet 86. Inflatable bladders 116 are removably supported in pocket 118 such as by VELCRO fastener components including a vertical strip or strips 122 suitably secured to the inner side of mesh fabric sheet 84 and cooperative components 124 each suitably secured to a corresponding one of the bladders 116. Preferably, each of the bladders 116 is independently inflatable and, for this purpose, each of the bladders is provided with a corresponding air flow tube 126 extending from one end thereof through slit 120 and to a valve block 128 which, as best seen in FIG. 10, is detachably secured to end 94 of the belt by a VELCRO fastening arrangement designated generally by the numeral 130. As will be appreciated from FIGS. 7, 8 and 10 of the drawing, valve block 128 includes a manifold passageway 132 and a tubular extension 134 providing an inlet thereto. Extension 134 extends through an opening therefor in belt end 94 so as to be exposed on the front side of the belt when the latter is applied about the waist of a wearer. In a well known manner, extension 134 is provided with an inflation-deflation valve 136 having a stem actuator 138 which, when pressed, communicates manifold 132 with ambient atmosphere. Thus, as is further well known, an air aspirator bulb 140 is adapted to be inserted into extension 134 to depress stem actuator 138 whereby compression of the aspirator bulb operates to pump ambient air into manifold passageway 132. Reversing the intake and discharge ends of aspirator bulb 140 relative to extension 134, or otherwise depressing stem actuator 138, provides for exhausting air from manifold 132.

Valve block 128 includes a plurality of valve elements each adapted to control the inflation and deflation of a corresponding one of the inflatable bladders 116. Any suitable valve arrangement can be provided for this purpose, whereby it will be appreciated that the following description of the valve shown in FIG. 10 is merely illustrative of one such arrangement. As will be appreciated from FIGS. 8 and 10, valve block 128 is provided with a plurality of outlet extensions 142 each receiving the tube 126 of a corresponding one of the inflatable bladders 116. Outlet 142 is coaxial with bores 144 and 146 extending through the valve block and manifold passageway 132, and bores 144 and 146 slidably support a valve stem 148 having an outer end provided with an actuating knob 150. The valve is open in the solid line position shown in FIG. 10, and the inner end of valve stem 148 is provided with an O-ring valve element 152 adapted to sealingly engage with bore 144 when the valve is closed as indicated by the broken line position in FIG. 10. Bore 146 is provided with an O-ring seal 154 sealingly engaging with stem 148 to prevent the leakage of air thereacross.

When the valve is open as shown by the solid line position in FIG. 10, compression of air aspirator bulb 140 in the manner described above operates to inflate the corresponding inflatable bladder 116 through the corresponding tube 126. It will be appreciated that any one or more of the inflatable bladders can be inflated at the same time by opening the valve therefor. When inflation is completed, valve 136 is operable to preclude deflation thereof but, preferably, valve stems 148 of the valves for the inflated bladders are displaced to the closed positions thereof to further assure against leakage from the bladder. When it is desired to deflate any one or more of the bladders, the corresponding valve is displaced to the open position and stem actuator 138 is depressed to provide for the air in the bladder or bladders to be exhausted thereacross to atmosphere.

It will be appreciated from the foregoing description that the bladder unit can be readily removed from the belt by separating valve block 128 from end 94, separating the bladders 116 from sheet 84 and then sliding the tubes and bladders from pocket 118 through slit 120. While it is preferred to secure bladders 116 within pocket 118 in the manner described, it will be appreciated that the bladders could be suitably mounted on a support plate slidable into and from pocket 118 or, alternatively, could be suitably interconnected with one another between the opposite ends thereof so as to be slidable into and from the pocket as a unit.

Bladders 116 are positioned perpendicular to the spine, and the independent inflatability thereof advantageously enables achieving system stabilization on varying degrees of firmness and softness as well as providing stabilization of specific vertebral levels by the inflation or deflation of different bladders, thus to meet the particular requirements of a patient. Further, the independent inflatability enables providing even pneumatic pressure against a magnet or magnets in pocket 104, provides even pneumatic support for hypo or hyperlordotic lumbar curves and stabilization of acute lumbosacral injury. The pneumatic bladder also biomechanically stabilizes hypermobile vertebral segments acting as a fulcrum to shift the instantaneous axis of rotation from the injury site.

Removability of the inflatable bladder section advantageously enables belt 78 to be used with a magnet or magnets only, with the inflatable bladders only, or with the latter in combination with a magnet or magnets. Further, while four inflatable bladders are shown in the embodiment herein disclosed, it will be appreciated that the belt can be provided with more or less than four bladders. It will likewise be appreciated that the belt can be provided with more than one pocket for receiving a magnet or magnets.

In the embodiments of FIGS. 1, 2, 5 and 7-9, the inner sheet of moisture absorbing wicking fabric facing the body of the wearer advantageously dissipates body heat and prevents moisture accumulation by absorbing perspiration, prevents chafing and provides an anti-bacterial/anti-fungul function.

While considerable emphasis has been placed herein on the preferred embodiments of the invention, it will be appreciated that other embodiments can be made and that changes can be made in the preferred embodiments without departing from the principles of the invention. In this respect, for example, the basic structure of the air inflatable belt can vary, especially with regard to the structure of the inflatable bladder section which could be a single bladder in the embodiment of FIGS. 1-6 rather than a plurality of interconnected bladder chambers. Moreover, it will be appreciated that fastening arrangements such as buckles can be employed for removably fastening the belt around a person's body. Further, in those embodiments including a pocket or pockets for removably receiving a magnet sheet, the pockets could be open on a side thereof rather than the top, and a plurality of pockets could be provided between the top and bottom edges of the belt as well as between the ends of the bladder section to further facilitate selectivity with respect to the location and field strength for the magnet sheet inserts. These and other changes in the embodiments disclosed herein will be suggested or obvious to those skilled in the art, whereby it is to be distinctly understood that the foregoing descriptive matter is to be interpreted merely as illustrative of the invention and not as a limitation.

Having thus described the invention it is claimed:

1. A lumbar support belt having opposite ends for releasably securing said belt about a person's body, inflatable bladder means supported between said opposite ends, said belt including inner wall means overlying said bladder means and facing the body of a person wearing said belt, and means providing said inner wall means with permanent magnet means producing magnetic field lines directed outwardly from said inner wall means toward said person's body, said bladder means being inflatable for exerting pressure against said magnet means to conform said inner wall means and said permanent magnet means to the contour of said body.

2. The belt according to claim 1, wherein said inner wall means includes pocket means and said means providing said inner wall means with permanent magnet means includes said pocket means and magnetic sheet means in said pocket means.

3. The belt according to claim 2, wherein said pocket means is open for removably receiving said magnetic sheet means.

4. The belt according to claim 2, wherein said magnetic sheet means includes sheet means of non-magnetic material having an active surface with permanent magnet particles of a ferrite material embedded therein.

5. The belt according to claim 4, wherein the particles in adjacent areas of said active surface are magnetized to provide north poles and south poles arranged in a geometric pattern establishing magnetic fields having angularities with respect to a line traversing said active surface.

6. The belt according to claim 5, wherein said geometric pattern is formed by concentric rings of alternating polarity.

7. The belt according to claim 2, wherein said inner wall means includes first sheet material means having an outer side facing said person's body and second sheet material means overlying said outer side and secured to said first sheet material means to provide said pocket means.

8. The belt according to claim 2, wherein said inner wall means has top and bottom edges, said pocket means extending between said edges and being open adjacent said top edge for removably receiving said magnetic sheet means.

9. The belt according to claim 8, wherein said magnetic sheet means includes sheet means of non-magnetic material having an active surface with permanent magnet particles of a ferrite material embedded therein and magnetized to provide north and south poles arranged in a geometric pattern establishing magnetic fields having angularities with respect to a line traversing said active surface.

10. The belt according to claim 9, wherein said sheet means of non-magnetic material is flexible and said geometric pattern is formed by concentric rings of alternating polarity.

11. The belt according to claim 8, wherein said inner wall means has opposite ends and said pocket means includes a plurality of separate pockets between said opposite ends of said inner wall means.

12. The belt according to claim 11, wherein each said pocket removably receives a corresponding magnetic sheet means.

13. The belt according to claim 12, wherein said magnetic sheet means includes sheet means of non-magnetic material having an active surface with permanent magnet particles of a ferrite material embedded therein and magnetized to provide north and south poles arranged in a geometric pattern establishing magnetic fields having angularities with respect to a line traversing said active surface.

14. The belt according to claim 13, wherein said sheet means of non-magnetic material is flexible and said geometric pattern is formed by concentric rings of alternating polarity.

15. The belt according to claim 12, wherein said inner wall means includes first sheet material means having an outer side facing said person's body and second sheet material means overlying said outer side and secured to said first sheet material means to provide said plurality of separate pockets.

16. The belt according to claim 1, wherein said inner wall means includes flexible, non-magnetic sheet means having a surface facing said person's body and said means providing said inner wall means with permanent magnet means includes permanent magnet particles of ferrite material embedded in said sheet means adjacent said surface and magnetized to provide adjacent areas of opposite polarity.

17. The belt according to claim 16, wherein said particles are magnetized to provide north and south poles arranged in a geometric pattern establishing magnetic fields having angularities with respect to a line traversing said surface.

18. The belt according to claim 17, wherein said geometric pattern is formed by concentric rings of alternating polarity.

19. The belt according to claim 18, wherein said non-magnetic sheet means has opposite ends and wherein a plurality of said concentric ring patterns are provided between said opposite ends of said non-magnetic sheet means.

20. The belt according to claim 1, wherein said inflatable bladder means is removably supported within said belt.

21. The belt according to claim 1, wherein said inflatable bladder means includes a plurality of inflatable bladder chambers, and means for inflating each of said chambers independent of one another.

22. The belt according to claim 21, wherein said means for inflating said bladder chambers includes valve means for each of said bladder chambers.

23. The belt according to claim 22, wherein said plurality of bladder chambers are removably supported within said belt.

24. The belt according to claim 23, wherein said valve means is removably supported on said belt.

25. The belt according to claim 1, wherein said inner wall means includes a wicking material sheet means for absorbing excess moisture.

26. The belt according to claim 25, wherein said inner wall means includes pocket means and said pocket means includes a wicking material sheet means for absorbing excess moisture at said person's body.

27. A lumbar support belt having opposite ends for releasably securing said belt about a person's body, inflatable bladder means supported between said opposite ends, said belt including inner wall means overlying said bladder means and facing the body of a person wearing said belt, means providing said inner wall means with flexible magnet means for producing magnetic field lines directed outwardly from said inner wall means toward said person's body, and means for varying the pressure exerted by said bladder means on said flexible magnet means and said body.

28. The belt according to claim 27, wherein said means for varying the pressure includes valve means for said bladder means.

29. The belt according to claim 27, wherein said bladder means includes a plurality of individual bladder chambers and said means for varying the pressure includes independent valve means for each chamber of said plurality of bladder chambers.

30. A lumbar support belt having opposite ends for releasably securing said belt about a person's body, a plurality of inflatable bladder means, each of said bladder means independently removably supported within said belt, said belt including inner wall means overlying said bladder means and facing the body of a person wearing said belt, flexible magnet means, pocket means on said inner wall means for said flexible magnetic means, and valve means connected to each of said bladder means for independently controlling pressure exerted by each said bladder means on said flexible magnetic means.

* * * * *